(12) United States Patent
Downing

(10) Patent No.: US 6,274,787 B1
(45) Date of Patent: Aug. 14, 2001

(54) TRANSPARENT, SPAN-OVER-THE-WOUND BANDAGE

(76) Inventor: Eric Downing, 30921 Orwell Rd., Ontario, WI (US) 54651

( * ) Notice: Subject to any disclaimer, the term of this patent is extended or adjusted under 35 U.S.C. 154(b) by 0 days.

(21) Appl. No.: 09/560,931

(22) Filed: Apr. 30, 2000

(51) Int. Cl.⁷ .................................................. A61F 13/00
(52) U.S. Cl. .................. 602/41; 602/2; 602/14; 607/96
(58) Field of Search .................... 607/96, 108; 602/2, 602/14, 41; 128/845, 847, 877–879, 888, 889; 604/164

*Primary Examiner*—Michael A. Brown
*Assistant Examiner*—Lalita M. Hamilton
(74) *Attorney, Agent, or Firm*—Michael I. Kroll

(57) ABSTRACT

A special bandaging device is provided which includes a canopy, of various shapes and sizes, which has a bottom edge for affixing to the patient's healthy skin surrounding the wound. Once affixed the canopy spans the entire wound without contacting the wound. Adhesive on the bottom edge is exposed after the removal of an adhesive backing, which prior to removal, encloses and hermetically seals the interior chamber of the canopy. The canopy can be formed in blister pack fashion from materials with varying degrees of malleability, with transparency being an available feature, such that the wound healing process can be monitored. An embodiment is provided which includes a fixed base portion that remains attached to the patient's skin, while the canopy is detachable for temporary access to the wound before the canopy is reattached. A locking ring on the canopy mates with a locking groove on the base for this purpose. Other embodiments include an elongated canopy for wounds having significant length. The elongated canopies can be open ended for trimming to precise length, or can be closed ended. Decorative overlays are provided which attach to the exterior of the canopy such that all or part of the wound is concealed. These overlays can be gummed for repeated attachment and removal.

2 Claims, 8 Drawing Sheets

TRANSPARENT, SPAN-OVER-THE-WOUND BANDAGE

BACKGROUND OF THE INVENTION

1. Field of the Invention

The present invention relates generally to bandages, and more specifically, to a transparent, self-adhering, span-over-the-wound bandage having a blister pack design to enclose a wound within a transparent, sterile, substantially hemispheric, protective bandage wherein only a peripheral base area having adhesive properties makes contact with the skin thereby eliminating the stretching and squeezing of the peripheral area of the wound that is common with conventional bandages. The present invention provides for constant monitoring of the injury from all angles without having to undress, redress, and stress the affected area. For aesthetic purposes the transparent span-over-the-wound bandage can come with decorative pieces of gummy paper to be placed over the bandage when visual inspection of the wound is not desired and can be easily removed as needed. The suspended nature of the bandage provides a sterile environment to promote the healing process and prevents pressure on the wound from contact that can irritate the injury caused by clothing, inadvertent touching, scratching, etc. The transparent span-over-the-wound bandage is manufactured of a non-penneable material that when properly applied forms a hermetically sealed containment chamber to protect the injury from airborne contaminants and water. The present invention is easier to apply than conventional bandages because the semi-rigid, hemispheric structure has no flapping ends that can roll up and stick together when tile adhesive backing is peeled off. The peel-off, adhesive backing also maintains the sterility of the bandage's inner surface by spanning across the open base area and all the peripheral contact edges until ready for use. The present invention could also have a two-piece configuration in which a blister pack canopy can be replaceably removed from an adhesive base to provide access to the wound in order to apply ointment or medicine without disturbing the injury or the adhesion of the base portion to the epidermal tissue. The transparent span over-the-wound bandage can come in a plurality of sizes and configurations including having a venting means to allow for flow through the bandage's interior. Furthermore, the present invention could be used as a protective covering for other items and uses such as restricting access to buttons on control panels or light switches et al. Two transparent span-over-the-wound bandages could also be affixed to one another's adhesive base to form a sealed disposable container to carry items such as pills or stool samples.

2. Description of the Prior Art

There are numerous bandages that provide for the protection of epidennal injuries. While these bandages may be suitable for the purposes for which they were designed, they would not be as suitable for the purposes of the present invention as heretofore described. It is thus desirable to provide a bandage having a transparent, self-adhesive blister pack style protective covering that has a non-penneable surface, a sterile interior surface and a peel off adhesive base. It is further desirable to provide a transparent, span-over-the-wound bandage that can be detachably fastened to a peel off self-adhesive base to allow for the application of a medicine or ointment and treatment of the affected area without disturbing the injury or the adhesion of the base to the skin.

SUMMARY OF THE PRESENT INVENTION

The present invention relates generally to bandages and, more specifically, to a transparent span-over-the wound bandage having a blister pack design wherein only the wider peripheral edges of the base area contact the surface to which the bandage is being applied while a narrower central portion remains elevated above the area to be protected.

A primary object of the present invention is to provide a transparent span-over-the wound bandage that will overcome the shortcomings of prior art devices.

Another object of the present invention is to provide transparent span-over-the wound bandages that are safe to use by providing a hermetically sealed, hygienic environment to promote the healing of a wound by protecting it from airborne contagions, water, and pressure from external sources Another object of the present invention is to provide transparent span-over-the-wound bandages that are fabricated of a non-permeable, malleable material that conforms to the surface being applied thereon wherein all peripheral edges of the bandage have an adhesive base to maintain the bandage to the aforementioned surface thereby forming a hermetically sealed chamber to contain the object to be protected.

A still further object of the present invention is to provide transparent span-over-the wound bandages that are easy to use because the semi-rigid qualities of the substantially dome-like form of the bandage make it easy to hold securely while peeling off the adhesive backing that covers the entire open base area including the adherent peripheral edges.

Still another object of the present invention is to provide a transparent span-over-the-wound bandage wherein the transparency of the bandage allows for accurate placement over the wound and the semi-rigid adhesive base applies pressure uniformly and simultaneously to the epidennal tissue surrounding the wound thereby preventing the stretching and squeezing and subsequent further traumatization of the injury that is common with conventional bandages.

A yet further object of the present invention is to provide transparent span-over-the wound bandages that have a sterile interior containment area which is maintained until ready to use by the adhesive backing that covers the entire open base area including the adherent peripheral edges.

Another object of the present invention is to provide transparent span-over-the wound bandages that allow for visual inspection of the wound or protected object while the bandage is in place.

Yet another object of the present invention is to provide transparent span-over-the wound bandages that have decorative pieces of gwmny paper to stick onto the exterior surface of the bandage to obstruct the view of the injury when visual contact is not desired.

Still another object of the present invention is to provide a transparent span-over-the-wound bandage having a venting means to allow fresh air to circulate through the bandage to promote the healing of the wound.

Another object of the present invention is to provide a transparent over-the-wound bandage having a venting means utilizing a filtration system to allow fresh air to circulate through the bandage while inhibiting the entrance of airborne particles therein.

Yet still another object of the present invention is to provide transparent span-over-the wound bandages that are comprised of an adhesive base section which mates with a replaceably detachable blister pack canopy to permit access to the injury without disturbing the integrity of the adhesive seal to the skin.

A yet further object of the present invention is to provide transparent span-over-the wound bandages wherein two bandages could be fastened together, adherent base to adherent base, to form an airtight container to carry items such as pills or stool samples.

A still further object of the present invention is to provide transparent span-over-the wound bandages that can be used to limit access to items such as control buttons or light switches.

Another object of the present invention is to provide transparent span-over-the wound bandages that can be of various sizes and configurations.

Additional objects of the present invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views.

FIG. 1 is a perspective view of the present invention in use showing a medical attendant applying transparent span-over-the-wound bandage to a child's injury. He has peeled off the protective adhesive backing and the semi-rigid properties of the blister pack allow him to hold the bandage securely in a manner that provides for application of the bandage without his hand making contact with the skin of the injured party thereby reducing the risk of infection. The transparency of the bandage allows for continuous visibility of the wound during application to assure proper placement of the present invention.

FIG. 2 is a perspective view of the present invention in use showing the bandage in place with the wound completely visible. The girl could now cover the injured area with her garment and not have to be concerned with friction from the garment being transferred through the bandage to the injury. The wound could now be monitored without the bandage being removed until the wound needs further treatment or has healed sufficiently to no longer need a protective covering.

DESCRIPTION OF THE REFERENCED NUMERALS

Figure 1:
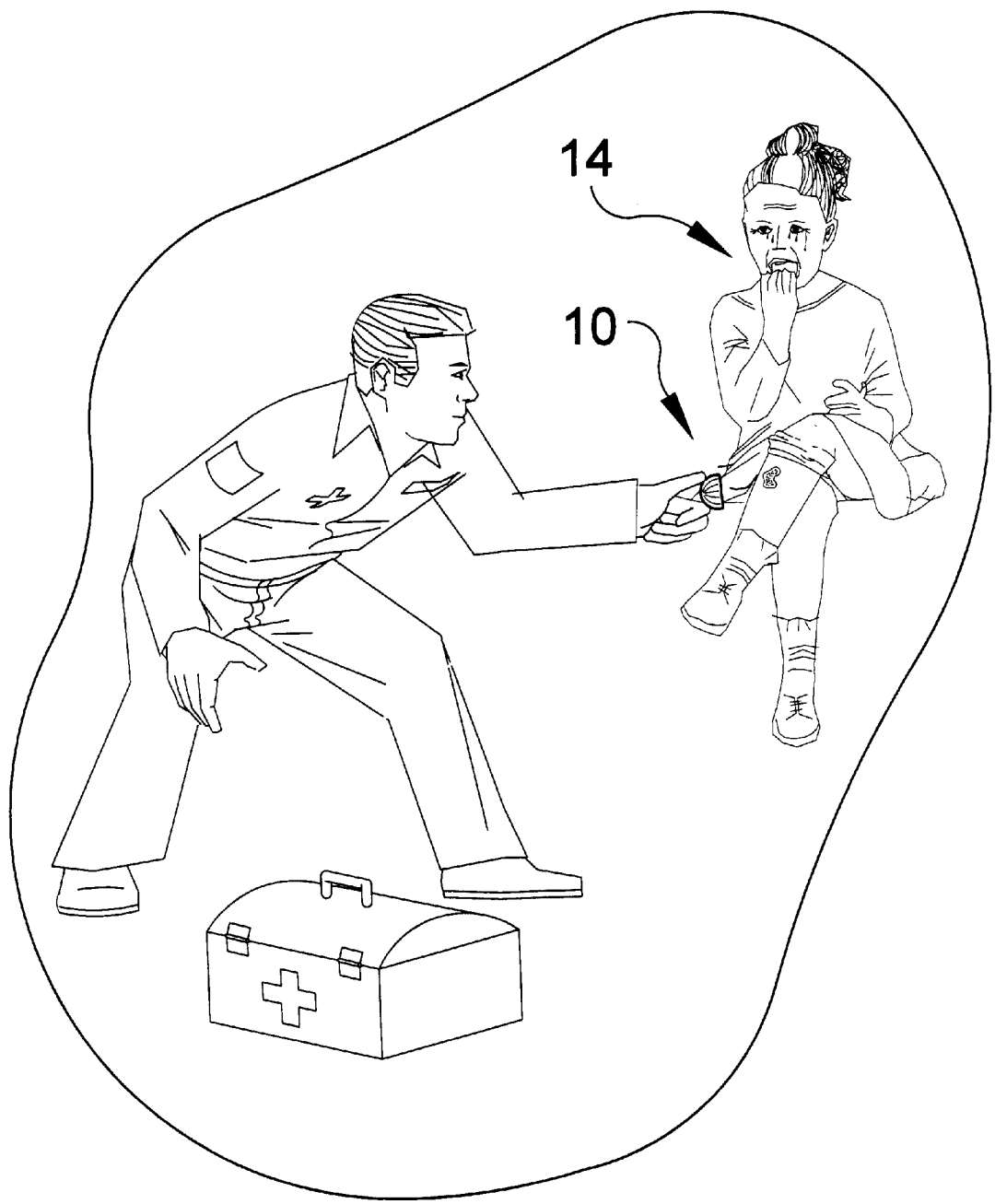
Figure 2:
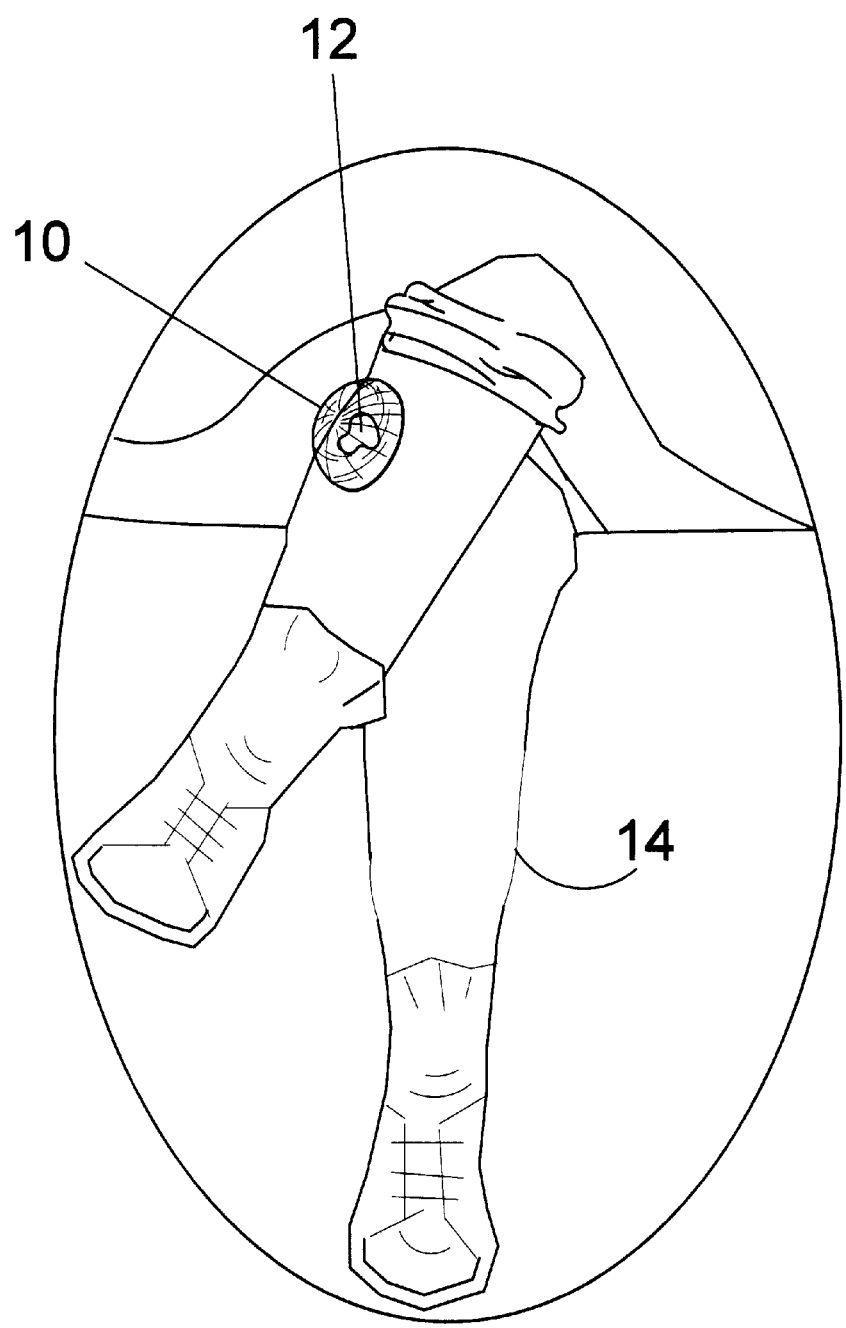

Turning now descriptively to the drawings, in which similar reference characters denote similar elements throughout the several views, the Figures illustrate the Transparent, Span-Over-the-Wound Bandage of the present invention. With regard to the reference numerals used, the following numbering is used throughout the various drawing figures.

| | |
|---|---|
| 10 | transparent, span-over-the-wound bandage of the present invention |
| 12 | wound |
| 14 | patient |
| 20 | canopy |
| 22 | canopy interior chamber |
| 24 | canopy bottom edge |
| 26 | canopy bottom edge adhesive |
| 28 | adhesive isolation member |
| 40 | base section |
| 42 | base bottom edge |
| 44 | adhesive isolation member for removable canopy |
| 46 | removable canopy |
| 48 | removable canopy bottom edge |
| 50 | base top edge |
| 52 | locking ring |
| 54 | locking groove |
| 56 | removable canopy interior chamber |
| 70 | vent |
| 72 | vent filtration element |
| 80 | elongated canopy |
| 82 | elongated canopy bottom edge |
| 84 | elongated canopy bottom edge adhesive |
| 86 | adhesive isolation member for elongated canopy |

DETAILED DESCRIPTION OF THE PREFERRED EMBODIMENT

Turning now descriptively to the drawings, in which similar reference characters denote similar elements throughout the several views, FIGS. 1 through 10 illustrate the Transparent, Span-Over-the-Wound Bandage of the present invention, indicated generally by the numeral 10.

The device 10 is shown in FIG. 1 being attached about the wound 12 on the patient 14. The attached device 10 is shown on the patient 14 in FIG. 2. As more particularly shown in FIGS. 3, 4 and 5, the device 10 includes a canopy 20 that is dome-shaped in this embodiment. In other embodiments, such as those shown in FIGS. 4A, 8, 9 and 10, the canopy 20 can be shaped differently, while continuing to elevate the bandage above the wound 12.

The canopy 20 is preferably made in a blister pack fashion from a nonpermeable, semi-rigid and transparent plastic, although a rigid embodiment is also provided, as well as, other embodiments with various degrees of malleability. The canopy 20 will have sufficient rigidity to retain its general shape, including the retention of its interior chamber 22, such that the bandage remains elevated above the wound 12.

The canopy 20 has a bottom edge 24 along the periphery of the canopy 20. The bottom edge 24 is shaped for the application of an adhesive 26 that is suitable for adhering to the patient's 14 skin.

Prior to attaching the device 10 about the wound 12, an adhesive isolation member 28 is attached to the canopy bottom edge 24. The adhesive isolation member 28 is in the form of a backing that extends across the bottom of the canopy 20, such that the canopy interior chamber 22 is hermetically sealed prior to the removal of the adhesive isolation member 28. As a result, the canopy interior chamber 22 is sterile prior to attachment about the wound 12.

In a typical application, an appropriately sized device 10 is selected from the available sizes. Following this selection the device 10 is prepared for placement about a wound 12 by removing the adhesive isolation member 28 and positioning the device 10 on the patient 14, such that the wound 12 is completely within the periphery of the canopy bottom edge 24. By pressing the device 10 to the patient's 14 healthy skin, the adhesive 26 attaches the canopy bottom edge 24 to such skin and isolates the wound 12. When so attached, the device 10 protects the wound 12 from contact with clothing and other objects during the healing process.

Figure 6:
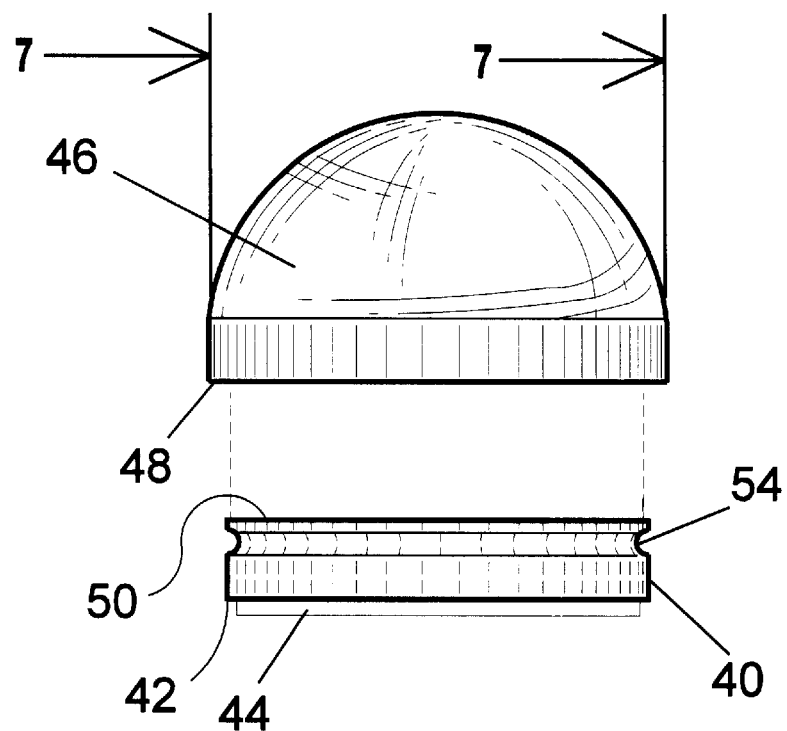
FIG. 6 is an exploded side view of a two piece configuration of the present invention showing the adhesive base section and the replacebly detachable blister pack canopy.
Figure 7:
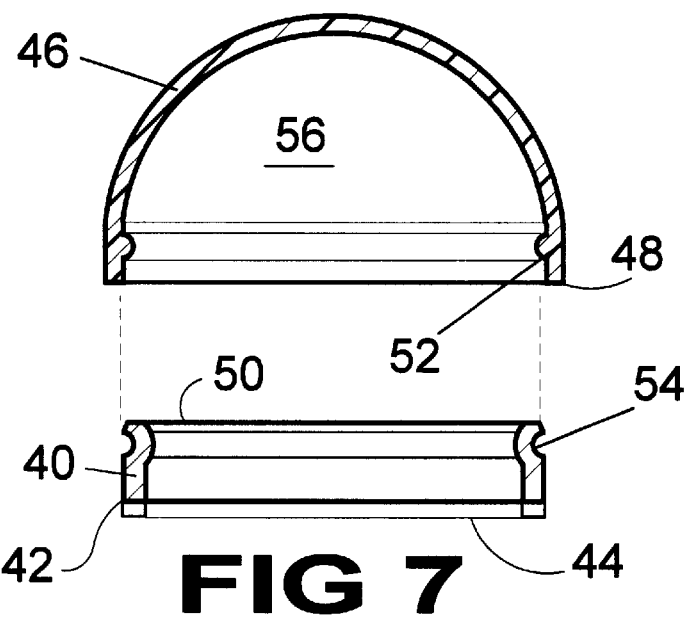
FIG. 7 is an exploded, cross-sectional side view of a two piece configuration of the present invention showing the adhesive base section and the replacebly detachable blister pack canopy. The locking means shown here constitutes a locking ring which snaps into a locking groove.

In another embodiment, shown in FIGS. 6 and 7, a base section 40 is provided which has a bottom edge 42 with an adhesive. An adhesive isolation member 44 is provided which, as above, extends completely across the base bottom edge 42. A removable canopy 46 has a bottom edge 48 that is detachably joinable to the base top edge 50. In this embodiment, a locking ring 52 proximate the canopy bottom edge 48 mates with a locking groove 54 that is proximate the base top edge 50. Other types of detachable joinder mechanisms are also available, in accordance with the present invention, and as determined by the intended end use for the overall device, as will occur to those of skill in the art upon review of the present disclosure.

In this latter embodiment, the locking ring 52 and locking groove 54 are mated prior to application to a wound 12. The adhesive isolation member 44 also remains attached prior to use, resulting in a hermetically sealed canopy interior chamber 56.

In actual use, the adhesive isolation member 44 is removed from the base bottom edge 42 and the base bottom edge 42 is positioned about the wound 12. After the base bottom edge 42 has adhered to the healthy skin of the patient 14, the wound 12 is isolated, until it becomes desirable to access the wound 12 for application of topical medicines, or for cleaning. When such access is desired, the canopy 46 is detached from the base 40. The canopy 46 can later be returned, and the wound 12 again isolated, by rejoining the locking ring 52 and the locking groove 54.

Figure 3:
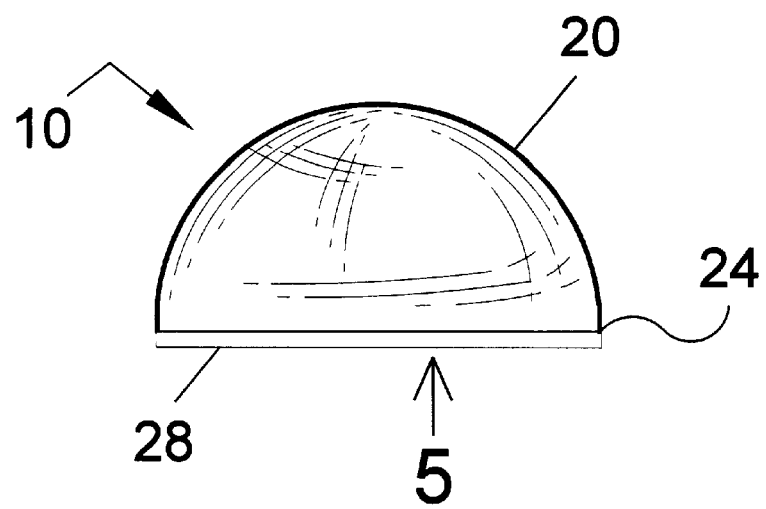
FIG. 3 is a side view of the present invention.
Figure 3A:
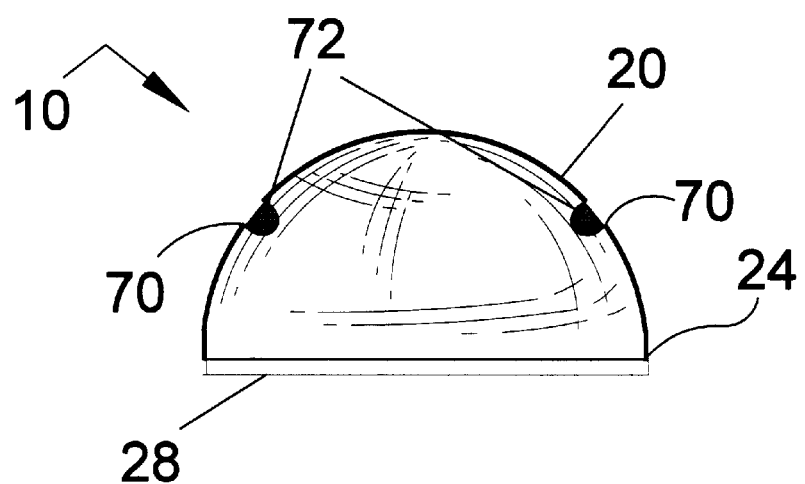
FIG. 3A is a side view of the present invention having a venting and filtration means to allow fresh air to flow through the area containing the wound while inhibiting the entry of airborne antigens.
Figure 4:
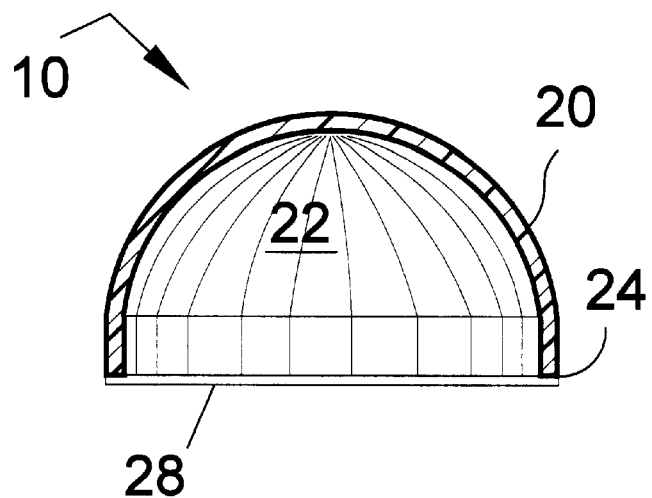
FIG. 4 is a cross-sectional side view of the present invention.
Figure 4A:
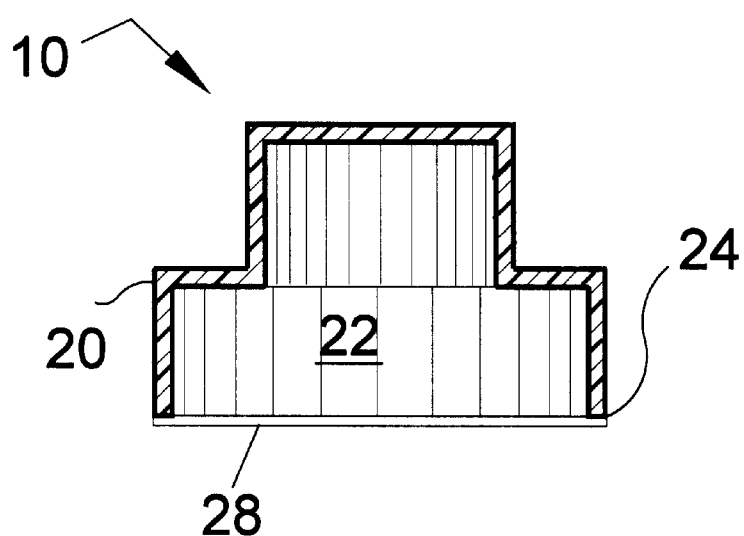
FIG. 4A is a side view of the present invention showing another possible configuration.
Figure 5:
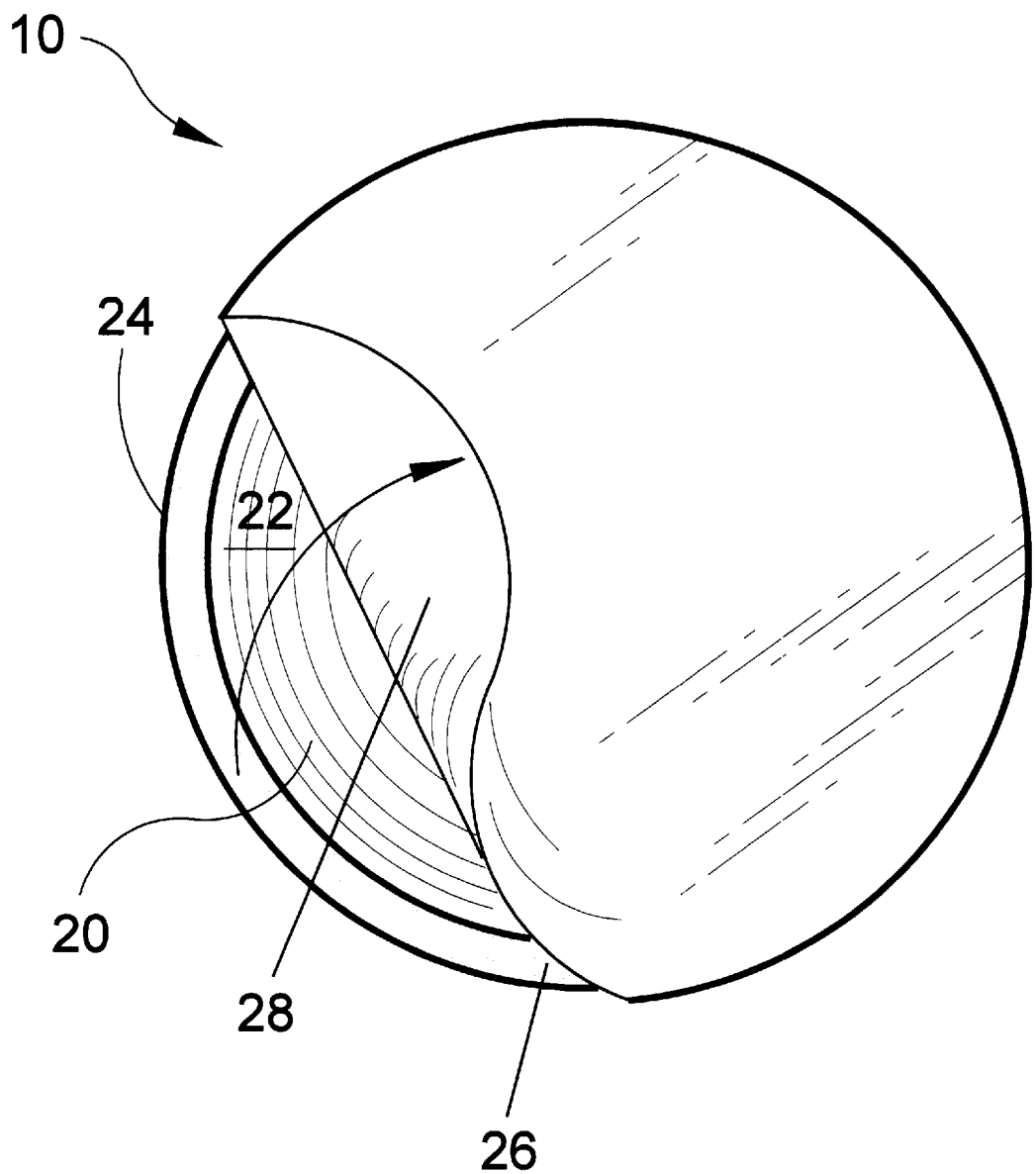
FIG. 5 is a bottom view of the present invention showing the protective peel off adhesive backing partially peeled away to reveal a section of the peripheral adhesive base area that contacts and adheres to the skin.

One or more air vents 70 are provided in other embodiments, as shown in FIG. 3A. These permit airflow while the device 10 continues to protect the wound 12 from clothing contact, etc. Micro-fiber and other filtration elements 72 can be positioned in such vents 70 to retain the sterile environment within the canopy interior chamber 22.

Figure 8:
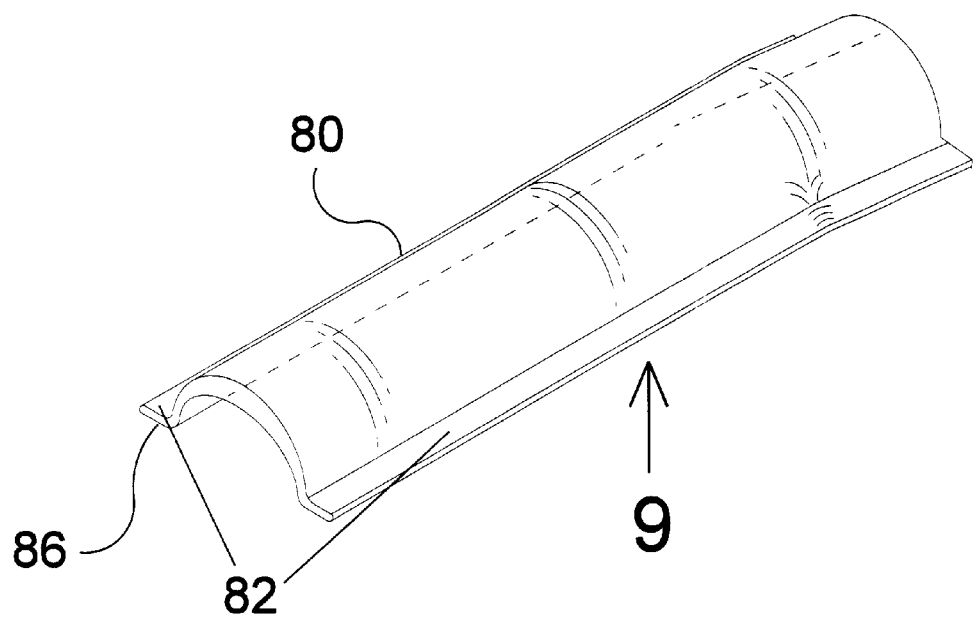
FIG. 8 is perspective view of an elongated version of the present invention.
Figure 9:
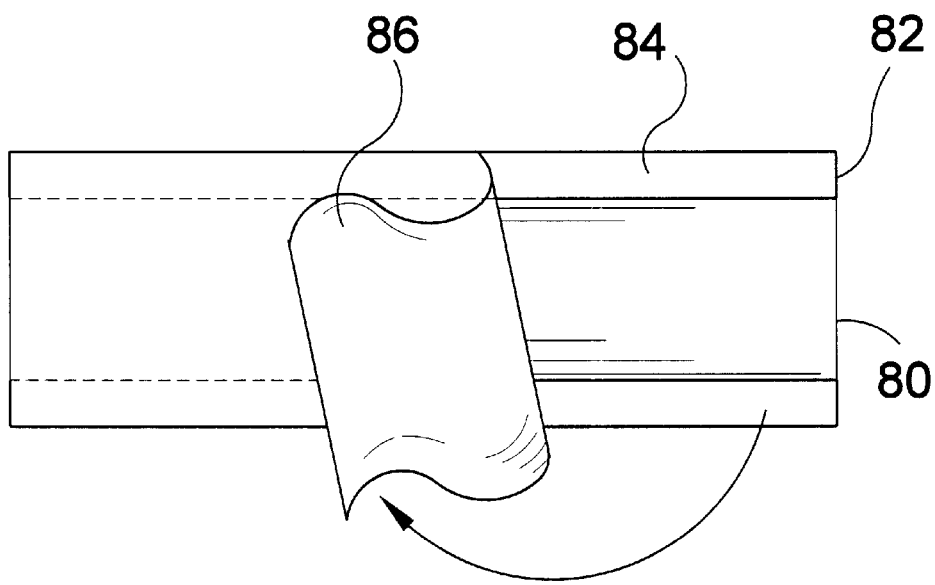
FIG. 9 is a bottom view of the present invention showing the peel off adhesive backing partially removed to reveal the adhesive.
Figure 10:
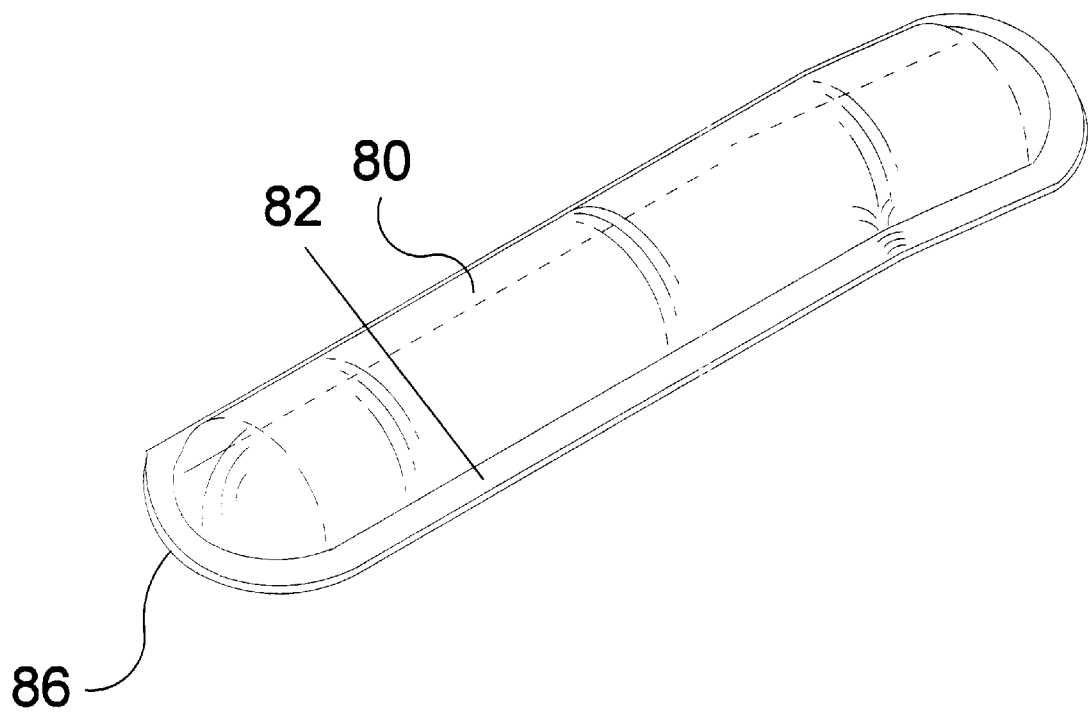
FIG. 10 is a perspective view of the embodiment of FIGS. 8 and 9, with closed ends.

FIGS. 8 and 9 depict an additional embodiment in which the canopy 80 is elongated such that it may be trimmed and fitted to wounds of particularly long length. If desired, isolation of the wound at the ends of the canopy 80 can be accomplished by applying conventional tape and or bandages. FIG. 10 depicts a canopy 80 with closed ends, which is provided in various fixed lengths for appropriate sizing to various wounds. Malleability is particularly desirable with respect to these embodiments. The canopy 80 in these embodiments has a bottom edge 82 with an adhesive 84 and an adhesive isolation member 86.

Overlays, including decorative overlays, are also provided which are gummed for repeated adhesion to the canopy 20. Such overlays (not shown) conceal the wound 12, either partially or completely. This improves the aesthetics of the device 10 during the period of healing.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A device for isolating a patient's flesh wound, comprising:

(a) a canopy, the canopy having a bottom edge;

(b) a base, the base having a bottom edge, the base bottom edge having an adhesive, the base further having a top edge, the base top edge being detachably joinable to the canopy bottom edge; and (c) an adhesive isolation member, the adhesive isolation member being removably attached to the base bottom edge adhesive such that the adhesive is isolated from adhesive contact with other objects until the adhesive isolation member is removed from the base bottom edge adhesive, the base bottom edge adhesive being adherable to human skin, such that when the adhesive isolation member is removed from the base bottom edge, and the bottom edge is brought into contact with the patient's skin, the attached canopy and base isolate the portion of the patient's skin having the wound, the base bottom edge being positioned with respect to the wound such that neither the base nor the canopy contact the wound.

2. The device of claim 1, wherein the base further comprises a locking groove proximate the base top edge, and wherein the canopy further comprises a locking ring proximate the canopy bottom edge, the locking groove and locking ring being sized for mating such that the base and canopy are detachably joinable.

* * * * *